United States Patent [19]
Della Valle et al.

[11] Patent Number: 5,210,185
[45] Date of Patent: May 11, 1993

[54] HUMAN NERVE GROWTH FACTOR

[75] Inventors: Francesco Della Valle; Lanfranco Callegaro; Silvana Lorenzi, all of Padova, Italy

[73] Assignee: Fidia S.p.A., Abano Terme, Italy

[21] Appl. No.: 322,729

[22] Filed: Mar. 13, 1989

[30] Foreign Application Priority Data

Mar. 18, 1988 [IT] Italy .................. 47745 A/88

[51] Int. Cl.$^5$ .................. A61K 37/00; C07K 3/02
[52] U.S. Cl. .................. 530/399; 530/851; 424/583
[58] Field of Search .................. 424/583; 514/2, 21; 530/851, 399

[56] References Cited

U.S. PATENT DOCUMENTS

| | | | |
|---|---|---|---|
| 4,407,744 | 10/1983 | Young | 530/399 |
| 4,659,696 | 4/1987 | Hirai et al. | 514/15 |
| 4,662,884 | 5/1987 | Stensaas | 623/12 |

FOREIGN PATENT DOCUMENTS

| | | |
|---|---|---|
| 0002139A | 5/1979 | European Pat. Off. |
| 0258111A | 3/1988 | European Pat. Off. |
| 0121338 | 8/1989 | European Pat. Off. |

OTHER PUBLICATIONS

P. Walker et al., Life Sciences, vol. 26 (1980) pp. 195–200.
L. D. Goldstein et al., Neurochemical Research, vol. 3 (1978) pp. 175–183.
D. J. Ennulat et al., Neurochemical Research, vol. 10, No. 7 (1985) pp. 1009–1014.
R. Levi-Montalcini et al., J. Exp. Zool., vol. 116 (1951) pp. 321–361.
S. Varon et al., Biochemistry, vol. 6 (1967) pp. 2202–2209.
R. H. Angeletti, Proceedings of the Natl. Acad. of Sci., vol. 65, No. 3 (1970) pp. 668–674.
G. P. Harper et al., Nature, vol. 279 (May 10, 1979) pp. 160–162.
P. Calissano et al., Hormonal Proteins and Peptides, vol. XII, pp. 2–56.
F. Hefti et al., Neuroscience, vol. 14, No. 1 (1985) pp. 55–68.
J. Scott et al., Nature, vol. 302 (Apr. 7, 1983) pp. 538–540.
A. Ullrich et al., Nature, vol. 303 (Jun. 30, 1983) pp. 821–825.
S. D. Skaper et al., Experimental Neurology, vol. 76 (1982) pp. 655–665.
U. K. Laemmli, Nature, vol. 227 (Aug. 15, 1970) pp. 680–685.
J. M. Gershoni et al., Analytical Biochemistry, vol. 131 (1983) pp. 1–5.
K. Stoeckel et al., Journal of Neurochemistry, vol. 26 (1976) pp. 1207–1211.
G. Kohler et al., Nature, vol. 256 (Aug. 7, 1975) pp. 495–497.
Methods in Enzymology, vol. XXII, "Enzyme Purification and Related Techniques", ed. W. B. Jakoby (1971) *enclosed cover & table of contents.
W. C. Mobley et al., Biochemistry, vol. 15, No. 25 (1976) pp. 5543–5552.
Remington's, "Remington's Pharmaceutical Sciences", 17th ed., Mack Publishing Co., Easton, PA, U.S.A., (1985) *enclosed cover & table of contents.
E. L. Fenton, Experimental Cell Research, vol. 59 (1970) pp. 383–392.
S. Varon, Discussions in Neurosciences, vol. 11, No. 3 (Oct. 1985).
E. Bigon et al., Neurochemical Research, vol. 15, No. 12, (1990) pp. 1197–1202.
Goding, Monoclonal Antibodies: Principles & Practice, Academic Press, New York, 1986, p. 219.
Goldstein et al., BA 66:64004, 1978.
Spectra/Por® Multiple Dialyzer, Spectrum Bio-Chromatography Products Catalog, 1990-1991, p. 130.
Centricon® Microconcentrators, Laboratory Separation Catalog Amicon 1987, p. 14.

Primary Examiner—Douglas W. Robinson
Assistant Examiner—Jean C. Witz
Attorney, Agent, or Firm—Birch, Stewart, Kolasch & Birch

[57] ABSTRACT

The present invention is directed to a method for the isolation of Human Nerve Growth Factor (HNGF) from human placenta. More particularly, the invention is directed to the method of isolation of the β-subunit of Human Nerve Growth Factor and Compositions containing the same for the treatment of neuropathological conditions.

7 Claims, 5 Drawing Sheets

HUMAN NERVE GROWTH FACTOR

The present invention is directed to human Nerve Growth Factor (hNGF) obtained by purification from human placenta and, more particularly, to a biological subunit (β-NGF).

BACKGROUND OF THE INVENTION

The Nerve Growth Factor (NGF) was originally discovered in mouse sarcoma tumors (Levi-Montalcini R. et al., J. Exp. Zool. 116:321, 1951) and was then purified to homogeneity from submandibular salivary glands of male mice (Varon S. et al., Biochemistry 6:2202, 1967) and from snake venom (Angeletti R. H., Proc. Natl. Acad. Sci. USA 65:668, 1970). Many other relatively rich sources of NGF have also been reported, including guinea pig prostate (Harper G. P. et al., Nature 279:160, 1979) and human placenta (Goldstein L. D. et al., Neurochem. Res. 3:175, 1978; Walker P. et al., Life Science 26:195, 1980; Calissano P. et al., Hormonal Prot. Peptides, XII:2, 1984). Small quantities of NGF have been reported to be present in other tissues including the mammalian central nervous system (Varon S., Discussions in Neuroscience, vol. II, n° 3, 1985; Hefti F. et al., Neuroscience 14:55, 1985). The physiological relationship between these potential sources of NGF and the apparent action sites is not very clear, but it is generally supposed that NGF is secreted by various peripheral tissues requiring innervation by those cells which respond to NGF.

The sequence and cloning of NGF obtained from submandibular glands of male mice were also carried out (Scott J. et al., Nature 302 538, 1983; Ulrich A. et al., Nature 303:821, 1983). The human βNGF gene has also been successfully isolated and cloned (Ulrich A. et al., Nature 303:821, 1983; European Patent n° 0121388).

NGF obtained from submandibular glands of mice was the type most completely characterized. NGF from mouse glands acts as a 7S proteic complex (molecular weight about 140,000 daltons) of three different subunits (α, β, γ) including $Zn^+$. The activity of NGF is exclusively associated with the subunit β (known as 2.5S NGF), a basic dimeric protein with a molecular weight of about 25,300 daltons (showing a molecular weight of about 12,650 daltons on electrophoresis with gel at high concentration of SDS and after its reduction with β-mercaptoethanol at 100° C. for 5 minutes), the isoelectric point of which is approximately 9.3. The amino acid sequences of β-NGF from submandibular glands of male mice and human provenience have been reported (Scott J. et al., Nature 302:538, 1983; Ulrich A. et al., Nature 303:821, 1983)

NGF from mouse submandibular gland was used for most of the studies on the activity of NGF in vivo and in vitro The range of biological activity in vitro of NGF has been determined both on primary neuronal cells and on clonal cells in cultures The primary neuronal cells reported as responding to NGF in vitro include fetal sensorial neurons (embryonic day 8–12) in dorsal root ganglia, noradrenergic fetal neurons in the sympathetic ganglia, cholinergic fetal neurons in the septum and adrenal chromaffin cells in development. While sensorial and sympathetic neurons depend on NGF for survival and development, cholinergic neurons do not seem to require NGF for survival, but only for their differentiation, that is to say, the expression of characteristic phenotypic traits bound to the neurotransmitter.

The addition of NGF to the adrenal chromaffin cells (cells derived the neural crest) in the initial stage of their development causes the expression of neuronal phenotypes. The clonal cells reported as responding to NGF in vitro include chromaffin suprarenal cells derived from tumors of the neuronal crest known as pheochromocytoma cells (PC12) and human neuroblastoma cells. After treatment with NGF these cells switch from a highly proliferous form of behaviour to a postmitotic neuronal state. Recently it has become possible to measure both NGF and its mRNA in several rat brain regions. A striking correlation of NGF level with the distribution of magnocellular cholinergic neurons has been found. Relatively high NGF levels in the range of those observed in peripheral sympathetic target tissues were found both in the regions innervated by magnocellular cholinergic neurons and in the regions containing their cell bodies, i.e. the hippocampus. The brain regions not related to the magnocellular cholinergic system contain considerably lower levels of NGF. The magnocellular cholinergic neurons of the basal forebrain project topologically to the neocortex, hippocampus and olfactory. The learning ability and the memory of the rodents have been associated with an age-dependent decline of cholinergic function in the forebrain and recent evidence indicates that the cholinergic neurons in the nucleus basalis magnocellularis, the septal-diagonal band area and the striatum undergo age-dependent atrophy. The spatial memory can be partly restored by intraventricular injection of NGF. This relation between the integrity of the basal forebrain cholinergic system and cognitive functions may also be valid for human beings. One of the main neuropathologic features of Alzheimer's disease is the drastic loss of magnocellular cholinergic neurons, although other transmitter systems undergo several changes. A correlation has been proposed between the extent of damage to the cholinergic system and the severity of the mental deficits.

The possible links between NGF and the pathophysiology and potential therapy of Alzheimer's disease have thus moved into the range of realistic consideration.

The involvement of the cholinergic system in the clinical manifestations of Alzheimer's disease is also supported by various experimental observations. For instance, in rats the interruption of the ascending cholinergic projections from the basal forebrain nuclei results in a marked reduction of memory and learning ability. These learning and memory deficiencies can be improved by injecting NGF into the hippocampus. The available pathophysiological information from Alzheimer patients, and the complementary information from animal experiments, open up interesting possibilities for the elucidation of the pathophysiological causes of Alzheimer's disease and potential new therapeutic approaches.

The availability of cDNA probes for human NGF, the possibility of producing human NGF by biotechnological methods, the consequent production of specific antibodies against human NGF, and the development of a specific enzyme immunoassay are all prerequisites for an experimental approach to the question as to whether Alzheimer's disease is actually associated with a deficit in the production of human NGF. If such a deficit were found, it would also be necessary to postulate that as well as a reduced production of NGF, there is also a reduced production of other, unknown neurotrophic factors acting on populations of neurons, which are also affected by Alzheimer's disease, but which are not responsive to NGF.

With respect to the therapeutic consequences, the benefits of NGF administration on learning deficits after experimental lesions of the cholinergic system suggest that, whatever the cause of the damage of the cholinergic neurons, an increased availability of NGF for these neurons either by exogenous application or by stimulation of endogenous production, could be substantial.

Since the production of human NGF by biotechnological methods is possible, potential immunological pitfalls of a therapy with non-human NGF could be eliminated.

For many years NGF research has been primarily based on NGF purified from the male mouse salivary gland and the antibodies produced against it. At a relatively early stage of NGF research it became apparent that the injection of anti-mouse NGF antibodies into chick embryos did not result in the same extensive destruction of the sympathetic nervous system as observed after antibody injections into newborn mice and rats. Since chick sympathetic and sensory neurons respond to mouse NGF in vivo and in vitro in a way similar to the corresponding mouse neurons, it was reasonable to conclude that the domain of the NGF molecule responsible for its biological activity must have been preserved, whereas other domains had changed during evolution. This assumption was further substantiated when bovine NGF was purified from bovine seminal plasma, and a detailed and comprehensive comparison between the biological activity of the mouse and bovine NGF became possible. These experiments demonstrated that the biological activity of mouse and bovine NGF were identical, although immunological cross-reactivity was very limited. The molecular cloning of mouse, human, bovine, and chick NGF, together with the amino acid sequence analysis of mouse NGF, has allowed comparison of the conserved and unconserved domains of these molecules and their relationship to biological activity and antigenicity. The overall conservation of NGF during evolution is remarkably high. Of the 118 amino acids of mature mouse $\beta$-NGF, only 16 amino acids were changed in bovine NGF, 19 in chick NGF, and 11 in human NGF. As was expected from previous observations, in the reduction of the three S—S bridges of mouse NGF one can obtain a complete loss of biological activity. The apparent discrepancy between the overall high conservation of the amino acid sequence and the poor immunological cross-reactivity is due to the fact that the amino acid changes between species are located in clusters. Hydropathy plots demonstrated that the changes are virtually exclusively located in the hydrophilic domains expected to be potential antigenic determinants. One single hydrophilic region has been shown to be strictly conserved in the NGF molecules of all species investigated so far. This conserved domain lends itself to future analysis by site-directed mutagenisis and by antibodies directed against synthetic peptides corresponding to this region.

The presence of three disulfide bonds in the correct conformation in the monomeric subunit of $\beta$-NGF represents a characteristic for this protein in terms of biological activity and immunogenicity.

Rigorous characterization between the native protein and DNA-derived product, both in the active form, is essential. Particular attention should be given to using a wide range of analytical techniques exploiting different physicochemical properties of the molecule; for instance, size, charge, isoelectric point, amino acid composition and hydrophobicity. It may be desirable to include suitable tests to establish that the product has the desired conformational structure and state of aggregation. Examples of techniques suitable for such purposes are: polyacrylamide gel electrophoresis; isoelectric focusing; size exclusion, reversed phase, ion exchange, hydrophobic interaction and affinity chromatography; peptide sequence mapping; amino acid analysis; light scattering; UV spectroscopy; circular dichroism, and other spectroscopic techniques. Additional characterization of the product using, for example, electron microscopy or immunochemical techniques may provide valuable information. Biological and immunological characterization should include as wide a range of techniques as is possible, appropriate to the anticipated biological activity. The determination of the specific activity of highly purified material will be of particular value (units of activity/weight of product).

While evaluating the potential pharmaceutical application of the human NGF ($\beta$ subunit) previously discussed and the Problems correlated with the DNA-derived first generation products, obtained in E. coli, the present inventors developed a scheme for the purification of NGF ($\beta$ subunit) from human placenta, potentially useful for large-scale applications. This material is characterized in terms of chemical, immunochemical and biological characteristics using the techniques and the reagents suitable for such purposes. Obviously, this purification scheme or only a single step can be applied to the purification of human NGF, obtained by means of recombinated DNA technology, which shows the same chemical, immunochemical and biological characteristics of NGF purified from human placenta.

Pharmaceutical compositions in accordance with the invention include $\beta$-NGF purified from human tissues, a $\beta$-NGF analog, biologically active fragments of $\beta$-NGF or of analog $\beta$-NGF, or nontoxic salts thereof, dispersed in a Pharmaceutically acceptable liquid or in a solid carrier. Such pharmaceutical compositions can be used in clinical medicine, both human and veterinary, in acute or chronic administrations for diagnostic or therapeutic purposes without problems of immunogenicity.

The present invention takes advantages:
  of the different isoelectric points of the native 7S complex and the $\beta$ subunit for the isolation and purification of $\beta$-NGF using cation exchange resins and
  of the cross-reactivity of human NGF ($\beta$ subunit) with the polyclonal antibodies produced against mouse NGF ($\beta$ subunit).

MATERIALS AND METHODS

In vitro studies were conducted utilizing "dissociated" fetal E8 chicken dorsal root ganglion cells (S. Skaper et al., Exp. Neurol. 76:655, 1982). The study of antibodies raised against murine NGF to inhibit the biological activity of NGF purified from human placenta was evaluated utilizing the above in vitro model system.

The purity of the NGF ($\beta$ subunit) from human placenta was evaluated utilizing the SDS slab electrophoresis technique (Laemmli U. K., Nature 227:680, 1970). The immunoreactivity was checked by the immunoblot technique (J. M. Gershoni et al., Anal. Biochem. 131:1, 1983).

Polyclonal antibodies against NGF were purified by affinity chromatography using 2.5S mouse NGF linked to Sepharose 4B (K. Stoeckel et al., J. Neurochem. 26:1207, 1976).

Anti-mouse NGF monoclonal antibodies were obtained by fusing the immunized rat spleen cells with mouse P3-X 63/AG8 myeloma cells (G. Köhler et al., Nature 256:495, 1975).

HUMAN β-NGF PURIFICATION

The isolation procedure was carried out as follows:

Step 1: The cotyledonal tissue of a single human placenta was homogenized with cold (4° C.) distilled-deionized water for 1-3 minutes at high speed in a Sorvall Amnimixer. The homogenate was centrifuged for 35 minutes. The supernatant was then lyophilized and resuspended in 0.02 M sodium phosphate buffer, pH 6.8, and dialyzed against two 4-liter lots of the same buffer solution for 16 hours at 4° C. All further steps were carried out at the same temperature.

Step 2: The dialyzed supernatant was mixed with a CM-cellulose resin equilibrated in 0.02 M phosphate buffer, pH 6.8, and the solid support washed with the same buffer until the absorbance of the eluate at 280 nm fell below 0.1. The eluated was then dialyzed against two 4-liter lots of .0.25 mM phosphate buffer, pH 6.8, over a period of 24 hours to reduce the buffering capacity of the solution.

Step 3: To the dialyzed solution was added one-ninth of its volume of sodium acetate buffer, pH 4.0, to rapidly reduce the pH and dissociate 7S NGF and establish a final buffer concentration of 0.05 M. Sufficient solid NaCl was added to bring the final concentration of NaCl to 0.4 M. After standing for 5 minutes to allow the precipitate to form, the solution was centrifuged at 27,000 g for 30 minutes, after having discarded the pellet.

Step 4: The acidified solution was immediately loaded onto a second CM-cellulose column equilibrated with 0.05 M sodium acetate buffer, pH 4.0, containing 0.4 M NaCl and the nonadsorbing material eluted from the column with 400 ml of the same buffer. After washing the column with 50 ml of 0.05 M sodium acetate buffer, pH 4.0, the remaining protein was eluted in two steps. Elution with 0.05 M Tris-HCl buffer, pH 9.0 (ca. 200 ml), produced a red-colored fraction containing half the remaining protein. The partially purified human NGF fraction was eluted last with 0.05 M Tris-HCl, pH 9.0, containing 0.5 M NaCl. The eluted material was dialyzed against 0.05 M sodium acetate, pH 5.0, 0.2 M NaCl overnight.

Step 5: The solution was centrifuged at 27,000 g for 15 minutes, and the supernatant was loaded onto a CM-cellulose column equilibrated with 0.05 M sodium acetate , pH 5.0, containing 0.2 M NaCl. The column was washed stepwise with 0.05 M sodium acetate, pH 5.0, containing 0.4 M NaCl and 0.5 M NaCl. The material associated with the biological activity was eluted from the column using 0.05 M sodium acetate, pH 5.0, containing 1.0 M NaCl. The material was dialyzed against 2-liter lots of 0.05 M sodium acetate, pH 5.5.

Step 6: The biological material was applied to a cationic exchange Mono S column equilibrated with 0.05 M sodium acetate, pH 5.5. The elution of the biological material was carried out using a gradient 0-1.0 M NaCl in 50 mM sodium acetate, pH 6.6. The flow rate was 1 ml/min. The protein associated with the biological activity was eluted in the time of range 26-30 minutes, with a salt concentration of 0.35-0.45 M NaCl. The material was dialyzed against 0.05 M sodium acetate, pH 5.0, containing 0.1 M NaCl.

Step 7: The biological material was applied to an affinity chromatography column with the anti-mouse NGF polyclonal antibodies coupled by a covalent method to the solid support. The column was washed extensively with the equilibration buffer of 0.05 M sodium acetate, pH 5.0. The bound human NGF was eluted with 0.1 M glycine-HCl, pH 2.5, containing 0.02% human serum albumin. Otherwise, alternatively:

Step 8: The biological material, loaded into an affinity column, was eluted with 0.05 M acetate buffer, pH 5.0, containing 4.5 $MgCl_2$. The purified human NGF (β subunit) was dialyzed against 0.05 M sodium acetate, pH 5.0, containing 0.1 M NaCl, and stored in aliquots at −80° C. until used.

Figure 1:
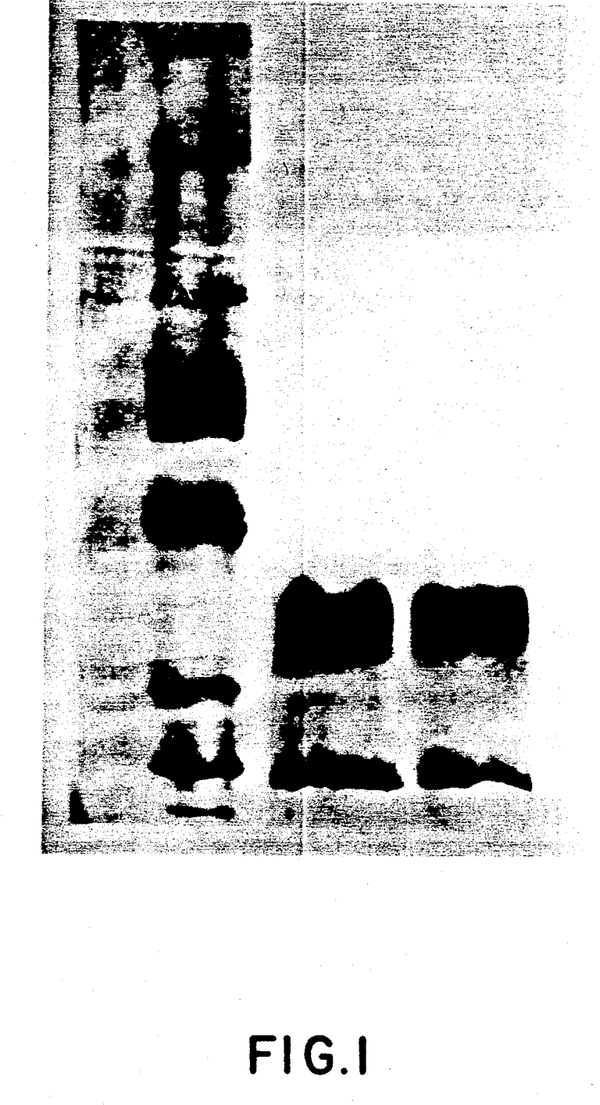
Figure 2:
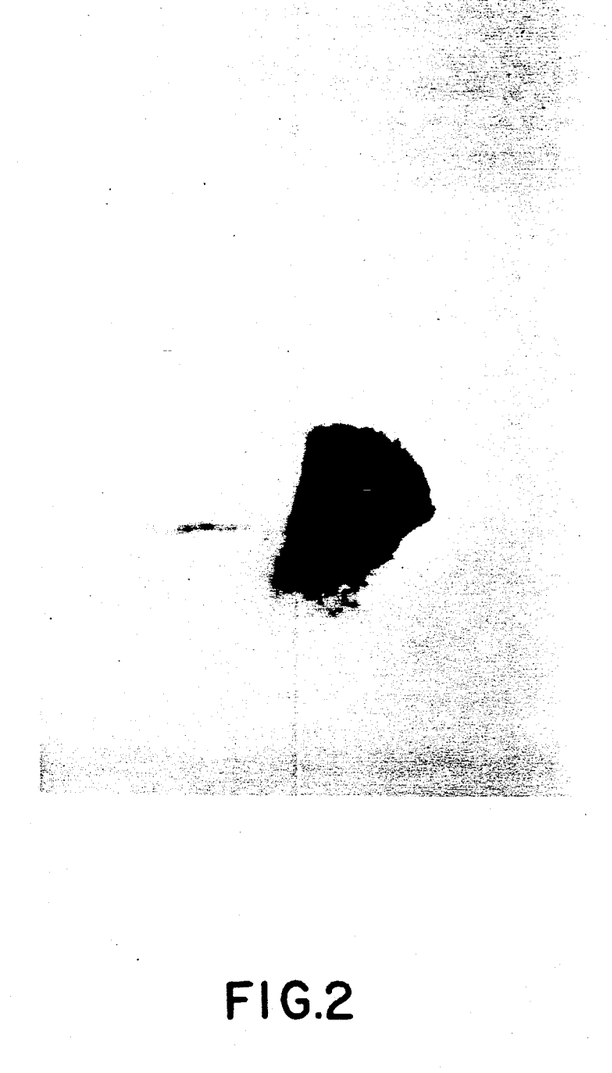

The chemical and immunochemical characteristics of hNGF biologically active subunit) purified from human placenta are:

a) the molecular weight of the purified material, evaluated by SDS gel eletrophoresis, was approximately 24.3-25.3 Kdaltons (FIG. 1);

b) the isoelectric point of this material was approximately 9.3-9.8;

c) by means of western blot technique, using a concentration (0.5 μg/ml) of affinity purified polyclonal antibodies produced against mouse NGF, the hNGF (β subunit) from human placenta showed a cross-reactivity against this reagent (FIG. 2).

by means of the same technique, the presence of this cross-reactivity was noted using a monoclonal antibody at the concentration of 2.0 μg/ml specific for the biological site of the mouse NGF.

Figure 3:
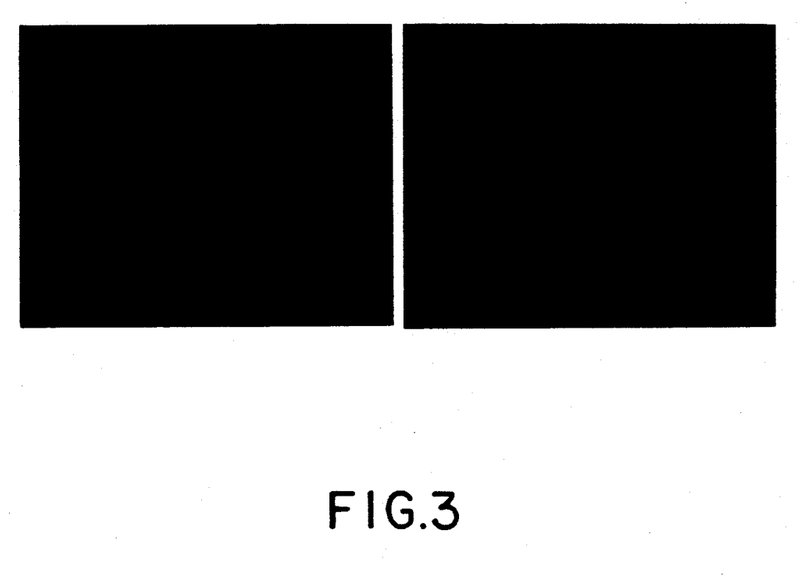

The hNGF (β subunit) purified from human placenta showed biological activity on DRG E8 (FIG. 3). The results shown in FIG. 3 were obtained in accordance with a procedure described in literature (S. Skaper et al., Exp. Neurol. 76:655, 1982).

Figure 4:
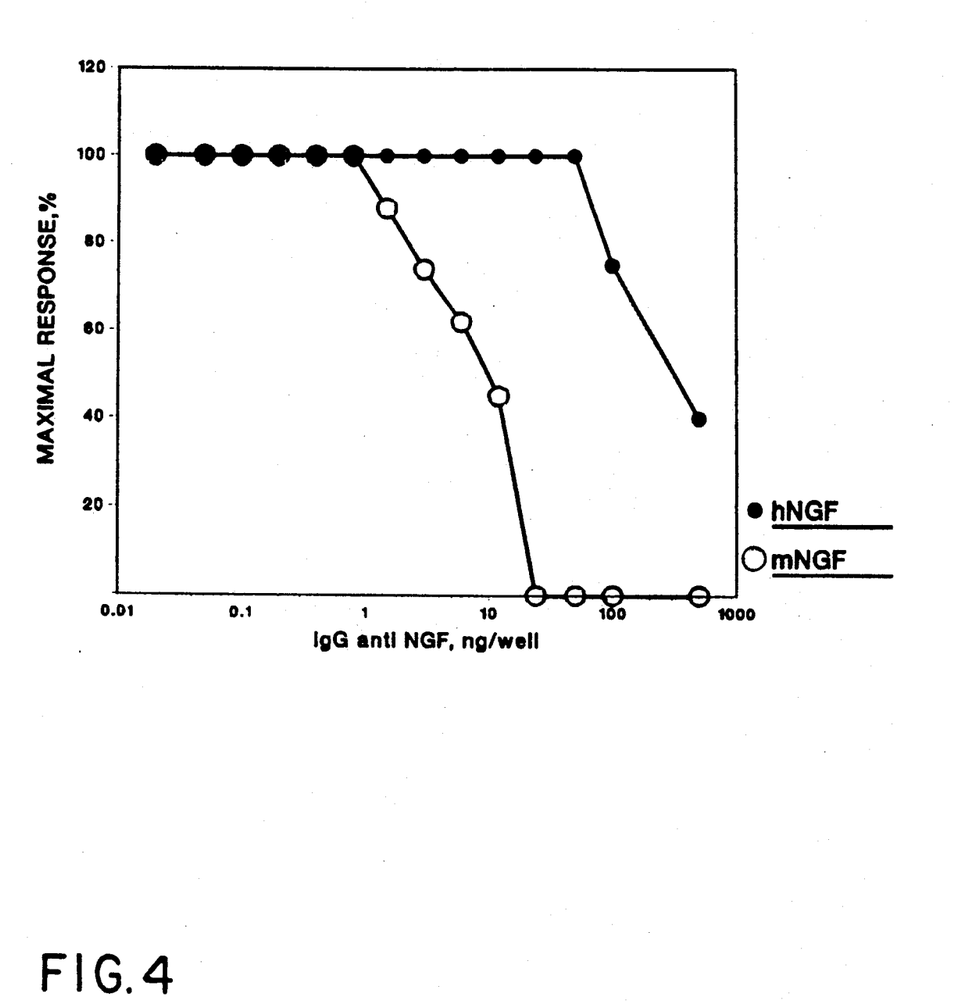
Figure 5:
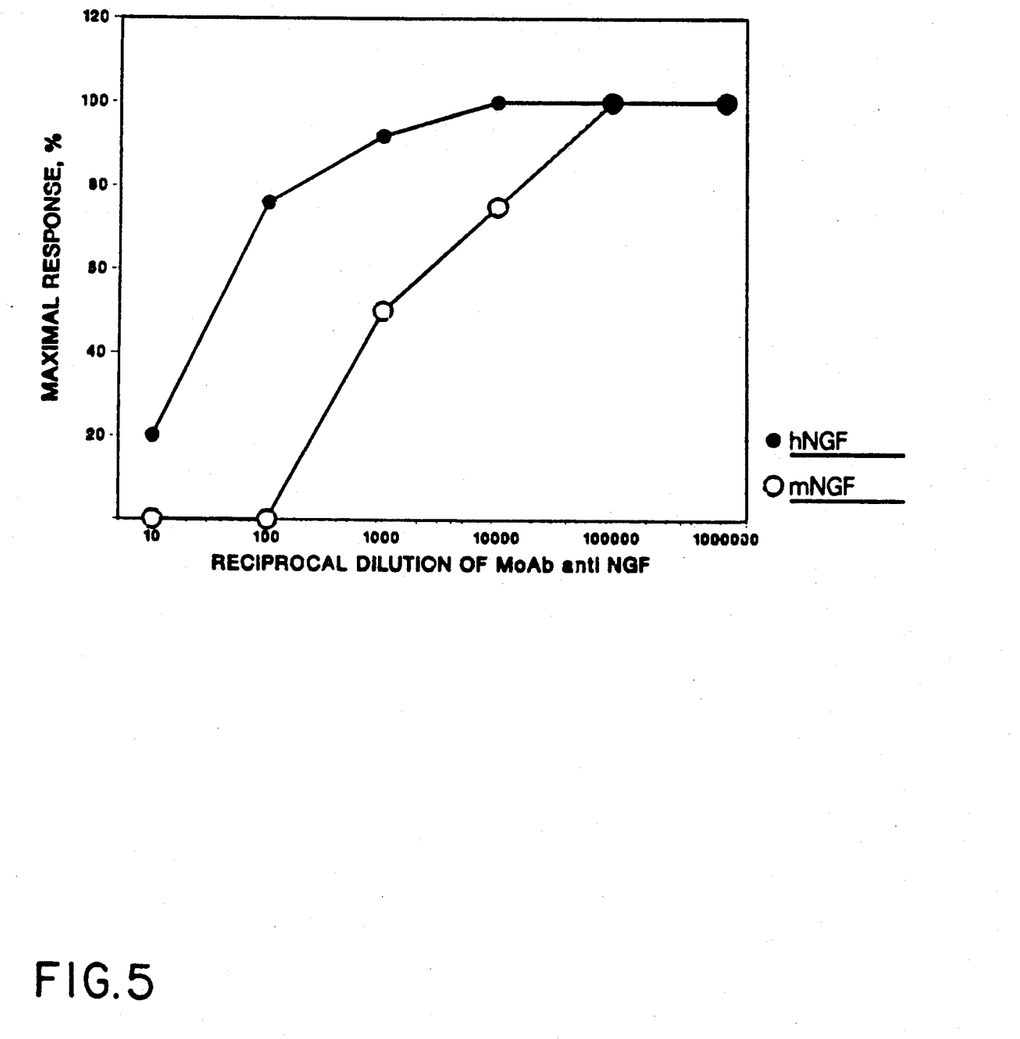

The biological activity due to hNGF from human placenta was inhibited by high concentration of affinity purified polyclonal antibodies (FIG. 4) and high concentration of the monoclonal antibody (FIG. 5). Generally speaking, the reaction conditions used for the purification steps employed in the present invention are those known in the art in connection with chromatographic methods utilized for the purification of proteins. Such methods are described in literature, for example in "Enzyme Purification and related Techniques", Edited by W. B. Jakoby, Section on Enzymes and Cellular Biochemistry, National Institute of Health, Bethesda, Md., Academic Press (1971); L. D. Goldstein et al., Neurochemical Research (3) 175-183 (1978); P. Walker at al., Life Sciences, Vol. 26, 195-200 (1980); W. C. Mobley et al., Biochem., Vol. 15, Nr. 25, 5543-5551; Pietro Calissano et al., Hormonal Proteins and Peptides, Vol. XII "The Nerve Growth Factor (NGF)". The purification steps may be carried out within a temperature range of 2° to 12° C.

PHARMACEUTICAL COMPOSITIONS

The formulation of pharmaceutical compositions containing the hNGF molecule (β subunit) derived from human placenta, described in this regard without and possibly also with gangliosides and phospholipids, includes methods already known for the preparation of pharmaceutically acceptable compositions suitable for effective administration to the patient, by means of which an effective amount of the hNGF molecule is combined in a mixture with a pharmaceutically acceptable vehicle. Suitable vehicles and their formulation inclusive of other proteins are described, for example, in the book "Remington's Pharmaceutical Sciences" (Remington's Pharmaceutical Sciences. Mack Publishing Company, Easton, Penna., USA 1985). These vehicles include injectable "deposit formulations".

Based on the above, the pharmaceutical formulation includes, although not exclusively, hNGF solutions or a freeze-dried powder of hNGF in association with one or more pharmaceutically acceptable vehicles or diluents, and contained in buffered media at a suitable pH and isosmotic with physiological fluids. Table 1 shows, for illustrative purposes only and without being limited by the same, the possible composition of formulations which may be prepared in the form of solutions for the treatment of nervous system disorders. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may be used for the pharmaceutical compositions of the hNGF molecule in isotonic solutions of the desired volume and include, but not exclusively, the use of buffered saline solutions with phosphate or citrate at suitable concentrations so as to obtain at all times isotonic pharmaceutical preparations of the desired pH, for example, neutral pH.

For illustrative purposes again, Tables 2 and 3 show some possible pharmaceutical compositions for the treatment of nervous system disorders. The pharmaceutical compositions set out in Tables 4A and 4B are preparations with two vials per single dose. The first vial contains the active substance with a composition by weight of about 0.01% to 50% of active substance together with a pharmacologically acceptable excipient, such as glycine or mannitol. The second vial contains a solvent prepared with the desired volume of phosphate or citrate buffered saline solution. The contents of the two vials are mixed immediately before administration, and the freeze-dried active substance dissolves rapidly to obtain an injectable solution. System No. 5).

The pharmaceutical formulation also includes, but without being limited to the same, suppositories for rectal administration with lipophilic, i.e., hydrosoluble, autoemulsive excipients of glyco-gelatine or other types. In these preparations the hNGF may be present in quantities varying between 0.01% and 1% by weight of the whole excipient. The suppository forms may contain, without being limited to the same, suitable quantities of acetylsalicylate.

Table 4 lists, for illustrative purposes only, possible suppository preparations for treatment of nervous system disorders.

Furthermore, the pharmaceutical preparations of hNGF both in freeze-dried form and as solutions may include phospholipids or gangliosides as discussed above in effective doses. For example, the doses may be (albeit not exclusively) similar to those generally used in man for the treatment of nervous system repair or complaints due to aging, respectively, and may depend on the administration route. The dosage of pharmaceutical preparations of hNGF and the timing of administration depend on the effect desired (determined by clinical trials) and the administration route, for example, the dosage and timing of administration may be similar (albeit not exclusively) to that commonly used on studies with other neuronotrophic agents.

TABLE 1

Examples of pharmaceutical compositions for injectable solutions.

| PREPARATION NO. 1 - one 2 ml ampoule contains: | |
|---|---|
| Active substance | μg 1 (2,500 BU) |
| Sodium chloride | mg 16 |
| Citrate buffer pH = 7 | ml 2 |
| in apyrogenic distilled water q.b. | |
| PREPARATION NO. 2 - one 2 ml ampoule contains: | |
| Active substance | μg 10 (25,000 BU) |
| Sodium chloride | mg 16 |
| Citrate buffer pH = 7 | ml 2 |
| in apyrogenic distilled water q.b. | |

The biological unit is defined as in the paper of Fenton E. L., Expl. Cell Res. 59:383, 1970.

TABLE 2

Examples of pharmaceutical composition systems

| SYSTEM NO. 1 | |
|---|---|
| a) One 2 ml vial contains: | |
| Freeze-dried active substance | μg 4 (10,000 BU) |
| Glycine | mg 30 |
| b) One 2 ml vial of solvent contains: | |
| Sodium chloride | mg 16 |
| Citrate buffer in water | ml 2 |
| apyrogenic distilled water q.b. | |
| SYSTEM NO. 2 | |
| a) One 2 ml vial contains: | |
| Freeze-dried active substance | μg 4 (10,000 BU) |
| Mannitol | mg 40 |
| b) One 2 ml vial of solvent contains: | |
| Sodium chloride | mg 16 |
| Citrate buffer in water | ml 2 |
| apyrogenic distilled water q.b. | |
| SYSTEM NO. 3 | |
| a) One 3 ml vial contains: | |
| Freeze-dried active substance | μg 10 (25,000 TU) |
| Glycine | mg 45 |
| b) One 3 ml vial of solvent contains: | |
| Sodium chloride | mg 24 |
| Citrate buffer in water | ml 3 |
| apyrogenic distilled water q.b. | |

TABLE 3

Examples of pharmaceutical composition systems.

| SYSTEM NO. 4 | |
|---|---|
| a) One 3 ml vial contains: | |
| Freeze-dried active substance | μg 10 (25,000 BU) |
| Mannitol | mg 60 |
| b) One 3 ml vial of solvent contains: | |
| Sodium chloride | mg 24 |
| Citrate buffer in water | ml 3 |
| apyrogenic distilled water q.b. | |
| SYSTEM NO. 5 (Example for subcutaneous injection) | |
| a) One 2 ml vial contains: | |
| Freeze-dried active substance | μg 5 (12,500 BU) |
| Glycine | mg 30 |
| b) One 2 ml vial of solvent contains: | |
| Sodium chloride | mg 16 |
| Citrate buffer in water | ml 2 |
| apyrogenic distilled water q.b. | |

TABLE 4

Examples of pharmaceutical compositions in the form of suppositories for the rectal route.

| PREPARATION NO. 1 | |
| --- | --- |
| Active substance | μg 10 (25,000 BU) |
| Cocoa butter | g 2.5 |
| PREPARATION NO. 2 | |
| Active substance | μg 10 (25,000 BU) |
| Carbowax 1540 | g 1.75 |
| Carbowax 6000 | g 0.75 |
| PREPARATION NO. 3 | |
| Active substance | μg 10 (25,000 BU) |
| Tween 61 | g 2.125 |
| Lanolin | g 0.25 |
| PREPARATION NO. 4 | |
| Active substance | μg 10 (25,000 BU) |
| Glycerine | g 1.5 |
| Water | g 0.75 |
| Gelatin | g 0.25 |

The invention being thus described, it will be obvious that these methods may be varied in many ways. Such variations are not to be regarded as departures from the spirit and scopes of the invention, and all such modifications as would be obvious to one skilled in the art are intended to be included within the scope of the following claims.

We claim:

1. A process for preparing a biologically active β subunit of human nerve growth factor from human placenta comprising the steps of:
   a) homogenizing the tissue of human placenta,
   b) centrifuging the homogenate and recovering the supernatant,
   c) dialyzing the supernatant at a pH of from 3.5 to 4.5 in order to dissociate the 7S NGF form,
   d) fractionating by chromatography the resultant solution on a three step cation exchange chromatography column, p1 e) purifying the active fraction obtained by cation exchange chromatography with a gradient of sodium chloride and pH from 5.5 to 6.5 and
   f) purifying the active fraction thus obtained by affinity chromatography on polyclonal antibodies, raised against mouse NFG.

2. A process according to claim 1, wherein step c) is conducted at pH 4.0.

3. A process according to claim 1, comprising eluting the active fractions from the cation exchange chromatography column with a gradient of sodium chloride, dissolved in 0.05 M acetate buffer and having a concentration of NaCl from 0 M to 1 M and a pH from 5.5 to 6.5.

4. A process according to claim 3, wherein the active fraction is purified by affinity chromatography on cross-reacting polyclonal antibodies, produced against mouse NGF β subunit.

5. A process according to claim 1, comprising conducting the process steps at a temperature from 2° to 12° C.

6. A process according to claim 1, comprising pooling together and freeze drying the active fractions.

7. A process according to claim 1, 2, 3, or 4, wherein at least one of the purification steps is applied for the purification of human nerve growth factor obtained by recombinant DNA technology.

* * * * *